US009983115B2

(12) United States Patent
Sieracki et al.

(10) Patent No.: US 9,983,115 B2
(45) Date of Patent: May 29, 2018

(54) SYSTEM AND METHOD FOR MONITORING PARTICLES IN A FLUID USING RATIOMETRIC CYTOMETRY

(71) Applicant: Fluid Imaging Technologies, Inc., Scarborough, ME (US)

(72) Inventors: Christian K. Sieracki, Edgecomb, ME (US); Peter Wolfe, Falmouth, ME (US); William H. Nelson, North Yarmouth, ME (US); Kent A. Peterson, Falmouth, ME (US)

(73) Assignee: Fluid Imaging Technologies, Inc., Scarborough, ME (US)

( * ) Notice: Subject to any disclaimer, the term of this patent is extended or adjusted under 35 U.S.C. 154(b) by 232 days.

(21) Appl. No.: 14/860,050

(22) Filed: Sep. 21, 2015

(65) Prior Publication Data

US 2017/0082530 A1 Mar. 23, 2017

(51) Int. Cl.
*G01N 15/14* (2006.01)
*G06T 7/00* (2017.01)
(Continued)

(52) U.S. Cl.
CPC ....... *G01N 15/147* (2013.01); *G01N 15/1429* (2013.01); *G01N 15/1434* (2013.01);
(Continued)

(58) Field of Classification Search
CPC ............. G01N 15/147; G01N 15/1429; G01N 15/1434; G01N 21/53; G01N 21/6486;
(Continued)

(56) References Cited

U.S. PATENT DOCUMENTS 3,508,830 A 4/1970 Hopkins et al.
3,764,512 A 10/1973 Greenwood et al.
(Continued)

FOREIGN PATENT DOCUMENTS

DE 69123990 7/1997
JP 2000338030 12/2000
(Continued)

OTHER PUBLICATIONS

Mosleh, Mogeeb AA, et al. "A preliminary study on automated freshwater algae recognition and classification system." BMC bioinformatics 13.17 (2012): S25.*
(Continued)

*Primary Examiner* — Amandeep Saini
(74) *Attorney, Agent, or Firm* — Caseiro Burke LLC; Chris A. Caseiro

(57) ABSTRACT

A particle detection system with a detection mechanism that includes detectors positioned to detect two different ranges of fluorescence produced by particles in the fluid in a flow chamber. Each of the detectors is arranged to generating a trigger signal whenever fluorescence is detected. The system and related method enhance the accuracy and sensitivity of blue-green algae monitoring by utilizing imaging flow cytometry combined with particle analysis and the measurement of the ratio of each particle's phycocyanin to chlorophyll b detected by using the two detectors configured for detection of two different fluorescence ranges, one associated with the phycocyanin and the other associated with the chlorophyll b. Captured images are be used in comparison to known images of a library of images using a support vector machine classifier.

17 Claims, 6 Drawing Sheets

(51) Int. Cl.
  *G01N 21/64* (2006.01)
  *G01N 21/53* (2006.01)
  *G06K 9/00* (2006.01)
  *G06K 9/62* (2006.01)
  *G01N 15/00* (2006.01)

(52) U.S. Cl.
  CPC ......... *G01N 15/1475* (2013.01); *G01N 21/53* (2013.01); *G01N 21/6486* (2013.01); *G06K 9/00147* (2013.01); *G06K 9/6269* (2013.01); *G06T 7/0004* (2013.01); *G01N 2015/0065* (2013.01); *G01N 2015/1486* (2013.01); *G01N 2015/1493* (2013.01); *G01N 2015/1497* (2013.01); *G01N 2021/6421* (2013.01); *G01N 2021/6482* (2013.01); *G01N 2201/12* (2013.01); *G06T 2207/30188* (2013.01)

(58) Field of Classification Search
  CPC ....... G01N 15/1475; G01N 2015/1493; G01N 2015/1486; G01N 2015/1497; G01N 2021/6482; G06K 9/00147; G06K 9/6269; G06T 7/0004
  USPC ......................................................... 382/224
  See application file for complete search history.

(56) References Cited

U.S. PATENT DOCUMENTS

| | | | |
|---|---|---|---|
| 4,407,008 A | 9/1983 | Schmidt et al. | |
| 4,412,246 A | 10/1983 | Allen et al. | |
| 4,612,614 A | 9/1986 | Deindoerfer et al. | |
| 4,661,225 A | 4/1987 | Penniman et al. | |
| 4,673,288 A | 6/1987 | Thomas et al. | |
| 4,778,593 A | 10/1988 | Yamashita | |
| 4,818,103 A | 4/1989 | Thomas et al. | |
| 4,902,137 A | 2/1990 | Krieg et al. | |
| 5,017,497 A | 5/1991 | de Grooth et al. | |
| 5,087,823 A | 2/1992 | Silvy et al. | |
| 5,117,466 A | 5/1992 | Buican | |
| 5,159,397 A | 10/1992 | Kosaka et al. | |
| 5,159,398 A | 10/1992 | Maekawa et al. | |
| 5,237,339 A | 8/1993 | Ichikawa | |
| 5,247,340 A | 9/1993 | Ohyama et al. | |
| 5,248,451 A | 9/1993 | Tsunaga et al. | |
| 5,311,290 A | 5/1994 | Olson et al. | |
| 5,448,349 A | 9/1995 | Kosaka | |
| 5,466,604 A | 11/1995 | Yang et al. | |
| 5,471,294 A | 11/1995 | Ogino | |
| 5,650,610 A | 7/1997 | Gagnon | |
| 5,689,110 A | 11/1997 | Dietz et al. | |
| 5,824,269 A | 10/1998 | Kosaka et al. | |
| 5,831,757 A | 11/1998 | DiFrancesco | |
| 5,850,284 A | 12/1998 | Schoeffler et al. | |
| 5,852,498 A | 12/1998 | Youvan et al. | |
| 6,028,663 A | 2/2000 | O'Mongain et al. | |
| 6,067,155 A | 5/2000 | Ringlien | |
| 6,115,119 A | 9/2000 | Sieracki et al. | |
| 6,211,956 B1 | 4/2001 | Nicoli | |
| 6,256,096 B1 | 7/2001 | Johnson | |
| 6,525,875 B1 | 2/2003 | Lauer | |
| 6,537,829 B1 | 3/2003 | Zarling et al. | |
| 6,674,058 B1 | 1/2004 | Miller | |
| 7,030,981 B2 | 4/2006 | Bishop et al. | |
| 7,221,503 B2 | 5/2007 | Eberhardt et al. | |
| 7,248,360 B2 | 7/2007 | Horchner et al. | |
| 7,271,897 B2 | 9/2007 | Wolleschensky | |
| 7,312,919 B2 | 12/2007 | Overbeck | |
| 7,532,326 B2 | 5/2009 | Corcoran | |
| 7,576,862 B2 | 8/2009 | Cromwell | |
| 7,599,545 B2 | 10/2009 | Shibata et al. | |
| 7,796,256 B2 | 9/2010 | Sieracki et al. | |
| 7,978,318 B2 | 7/2011 | Ilkov | |
| 8,005,314 B2 | 8/2011 | Ortyn et al. | |
| 2002/0135752 A1 | 9/2002 | Sokolov et al. | |
| 2004/0157231 A1 | 8/2004 | Meltola et al. | |
| 2005/0030373 A1 | 2/2005 | Chao et al. | |
| 2005/0037517 A1 | 2/2005 | Anderson et al. | |
| 2006/0017001 A1 | 1/2006 | Donders et al. | |
| 2006/0044548 A1 | 3/2006 | Lee et al. | |
| 2006/0177937 A1 | 8/2006 | Kurabayashi et al. | |
| 2006/0197032 A9 | 9/2006 | Oostman, Jr. et al. | |
| 2007/0139541 A1 | 6/2007 | Fein et al. | |
| 2007/0184471 A1 | 8/2007 | Yguerabide et al. | |
| 2008/0123169 A1 | 5/2008 | Sutko et al. | |
| 2008/0192231 A1 | 8/2008 | Jureller et al. | |
| 2009/0107913 A1 | 4/2009 | Johnson | |
| 2009/0125242 A1 | 5/2009 | Choi et al. | |
| 2009/0174703 A1 | 7/2009 | Hermanson et al. | |
| 2009/0252414 A1 | 10/2009 | Suzuki | |
| 2009/0273774 A1 | 11/2009 | Sieracki et al. | |
| 2009/0283697 A1* | 11/2009 | Sieracki | G01N 15/1434 250/458.1 |
| 2009/0289187 A1 | 11/2009 | Mian | |
| 2010/0027007 A1 | 2/2010 | Adams et al. | |
| 2011/0195492 A1 | 8/2011 | Sharpe et al. | |
| 2011/0200954 A1 | 8/2011 | Sassow | |
| 2012/0002029 A1 | 1/2012 | Sieracki et al. | |
| 2012/0127298 A1 | 5/2012 | Sieracki et al. | |

FOREIGN PATENT DOCUMENTS

| | | |
|---|---|---|
| KR | 20120061551 | 6/2012 |
| WO | 1997040181 | 10/1997 |
| WO | 2000004371 | 1/2000 |
| WO | 2007119263 | 10/2007 |
| WO | 2008100704 | 8/2008 |

OTHER PUBLICATIONS

Notification of International Search Report and Written Opinion in PCT application No. PCT/US2009/02562, dated Jul. 17, 2009, 7 pp.

Oldenbourg, R., Methods in Molecular Medicine: Analysis of Microtubule Dynamics of Polarized Light, Methods Mol. Med. 2007, 137, 111-123, US.

Johnson, L., Enhanced early detection and enumeration of zebra mussel (*Driessna* spp.) veligers using cross-polarized light microscopy, Hydrobiologica, 1995, 312, Belgium.

Marie, D. et al., Enumeration of Marine Viruses in Culture and Natural Samples by Flow Cytometry, Applied and Environmental Microbiology, Jan. 1999, vol. 65, No. 1, 45-52, US.

Website page mccroneassociates.com/Techniques/detailasp?TECHNIQUES_ID=19& of McCrone Associates, 1 pp.

Kay, DB et al., Imaging in Flow, Journal of Histochemistry and Cytochemistry, vol. 27, No. 1, pp. 329-334, 1979.

Notification of International Search Report and Written Opinion in PCT application No. PCT/US2013/042285, dated Nov. 12, 2013, 9 pp.

International Search Report and Written Opinion for PCT Application, PCT/US2013/071781, dated Apr. 17, 2014, 7 pages.

Levi, Valeria, QiaoQiao Ruan, and Enrico Gratton. "3-D particle tracking in a two photon microscope: application to the study of molecular dynamics in cell." Biophysical Journal 88.4 (Apr. 2005): 2919-2928.

Kis-Petikova, Katarina, and Enrico Gratton. "Distance measurement by circular scanning of the excitation beam in the two-photon microscope." Microscopy research and technique 63.1 (2004): 34-49.

Levi, Valeria, et al. "Scanning FCS, a novel method for three-dimensional particle tracking." Biochemical Society Transactions 31.5 (2003): 997-1000.

Bräuchle, Christoph, Don Carroll Lamb, and Jens Michaelis, eds. Single particle tracking and single molecule energy transfer. John Wiley & Sons, Dec. 21, 2009, two sections, 44 pp.

Supplementary European Search Report and European Search Opinion for European Patent Application, 13794574.7, dated Apr. 30, 2015, 7 pages.

(56) References Cited

OTHER PUBLICATIONS

Transmittal regarding foreign literature, dated Jan. 29, 2016, 2 pages.

* cited by examiner

SYSTEM AND METHOD FOR MONITORING PARTICLES IN A FLUID USING RATIOMETRIC CYTOMETRY

BACKGROUND OF THE INVENTION

1. Field of the Invention

The present invention relates generally to a flow analysis configuration used in particle analysis instrumentation, and more particularly to a flow analysis system configured to enable the accurate identification of the existence of blue-green algae in a fluid. The system may include an optical imaging capability.

2. Description of the Prior Art

The art has seen various optical/flow systems employed for transporting a fluid within an analytical instrument to an imaging and optical analysis area. A liquid sample is typically delivered into the here of a flow chamber and this sample is interrogated in some way so as to generate analytical information concerning the nature or properties of the sample. For example, a laser beam may excite the sample that is present in the bore of the capillary, with the emitted fluorescence energy representing the signal information.

In the area of identifying specific particles in a flowing fluid, the closest known relevant technological developments involve bulk measurements or conventional flow cytometry, neither of which is sufficient to enable the detection of blue-green algae early enough to initiate steps to eliminate it within a desired period of time. It would be advantageous to detect with accuracy the existence and density of blue-green algae in a flowing fluid to improve the taste of drinking water. The existing bulk-detection technology requires the existence of a minimum amount of the algae before detection can occur. Unfortunately, that capability is not satisfactory as the blue-green algae cannot be detected before it becomes a noticeable problem.

The inefficiencies of detecting blue-green algae with existing bulk monitoring and conventional flow cytometry systems produce inconclusive resolution resulting from less than optimum collection of fluorescence emissions from a fluid sample passing through the bore of the flow chamber. Conventional flow cytometers involve the use of flow nozzles that limit the size of particles passing into the flow chamber for detection. For example, particles greater than 60 micrometers ($\mu m$) in cross section will clog the nozzle. Blue-green algae clumps and, as a result, particle sizes of 100 $\mu m$ to 2000 $\mu m$ in cross section are common. They also exceed the maximum internal dimensions of the nozzle. To date, therefore, the particle detection art, including the imaging and/or flow cytometry art has not disclosed utilizing sufficient arrangements for optimizing particle delivery, particle resolution and fluorescence emission collection suitable to produce accurate blue-green algae detection at low concentration levels. There is therefore a need in the art for a system and related method to improve blue-green algae detection, including in a flowing fluid and with or without imaging of the algae.

SUMMARY OF THE INVENTION

It is an object of the present invention to provide a system arranged to detect with reliable accuracy the existence of blue-green algae in a fluid. It is also an object of the present invention to provide such a system that may be incorporated into, or operate in a similar manner as that of, existing detection system including, but not limited to, imaging flow cytometers.

These and other objects are achieved with the present invention, which is a cytometer system with a detection mechanism that includes detectors configured to detect two different ranges of fluorescence produced by particles, including blue-green algae particles, in the fluid flowing through the flow chamber. Each of the detectors is arranged to generate a trigger signal whenever fluorescence is detected. Also, the system includes an arrangement that permits particles much larger in size to pass through the field of view than permitted by current flow cytometry systems. This ensures more accurate blue-green algae detection as more particles actually in the fluid under evaluation will be delivered into the field of view. It is to be noted that the length and width of the channel of the chamber are preferably selected to roughly match the field of view of the imaging and fluorescence optics used to detect the particles. The system further optionally includes a video system arranged to image particles in the fluid in the flow chamber in response to the trigger signals. Images captured by the video system are of high resolution and may be used in comparison to known blue-green algae images of a library of images. Computer programming is created to operate a computing device of the system to distinguish particles in the fluid based on different fluorescence emission characteristics. Further, the programming may optionally be configured to match (or recognize non-matching) of captured images with known particles, including blue-green algae particle images of the library. Identification of blue-green algae in the fluid may then be made.

The system and related method of the present invention enhances the accuracy and sensitivity of blue-green algae monitoring by utilizing particle analysis and the measurement of the ratio of each particle's phycocyanin to chlorophyll b. For the blue-green algae as an example, an individual blue-green algae particle's phycocyanin to chlorophyll b content may be determined using the two detectors configured for detection of two different fluorescence ranges, one associated with the phycocyanin and the other associated with the chlorophyll b. The system and related method may also be utilized to image the particle and additional particle analysis may be performed by comparison of the captured images with the library of known images.

The present invention provides for the imaging of particles in a flowing fluid wherein two channels are used that have differing spectral sensitivities to the particles that is used to trigger a camera. The ratios between the spectral sensors is used as the trigger, otherwise noted as emissions radiometry, the pigments in the desired bacteria used as the means for sensing their presence and causing the camera to be activated. Thus, the dual channel system allows for precise imaging of desired bacteria in a fluid flow with a high incidence of accuracy. The advantages gained by the invention compared to the state of the art of currently available particle-in-fluid detection systems are: 1) greater certainty of total particle transfer to the field of view; 2) more accurate particle identification, including blue-green algae particle detection from individual cell fluorescence ratios and, optionally, image matching to image libraries of known particles; and 3) better ability to detect smaller or weaker fluorescent particles versus conventional bulk fluorescence techniques. These and other advantages of the present invention will become more readily apparent upon review of the following detailed description, the accompanying drawings and the appended claims.

DETAILED DESCRIPTION OF THE PREFERRED EMBODIMENT

Figure 1:
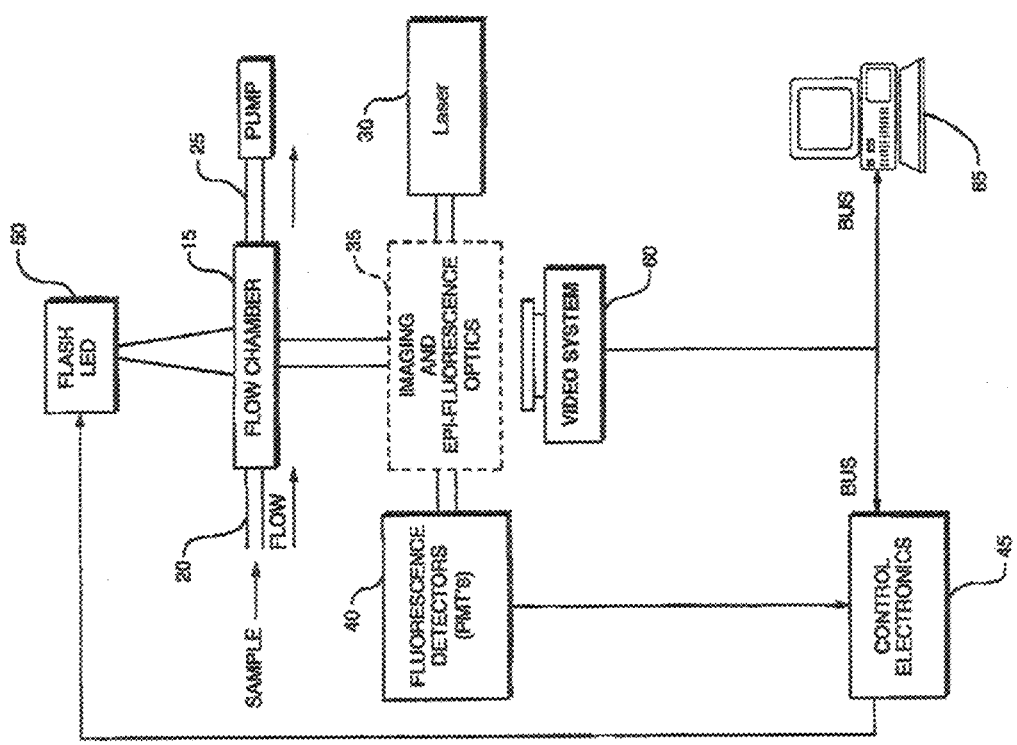
FIG. 1 schematically illustrates a system for studying particles in a fluid according to one embodiment of the invention.
Figure 2:
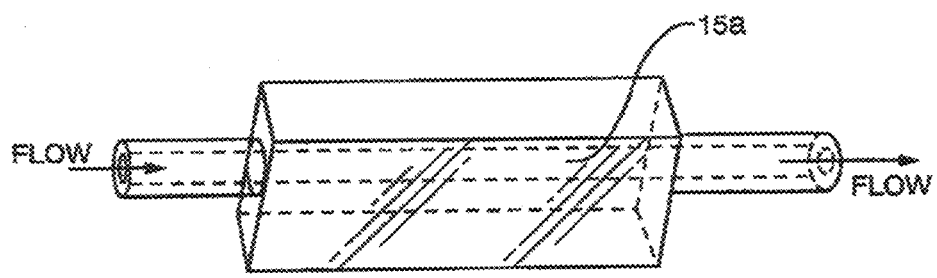
FIG. 2 is an enlarged perspective view of the flow chamber of the system of FIG. 1.

A system 10 of the present invention suitable for high quality automated counting and imaging of particles that exist in a fluid is shown in FIGS. 1 and 2. The system 10 of the present invention is similar in manner to the flow cytometer described in U.S. Pat. No. 6,115,119 entitled "Device And Method For Studying Particles In A Fluid/" issued Sep. 5, 2000, the entire content of which is incorporated herein by reference. The system 10 includes a flow chamber 15, a light source 30, imaging and fluorescence optics 35, an image detection system 40, a backlighting generator 50, an optional image capturing system 60 and a computing device 65. The combination of these components of the system 10 arranged and configured as described herein enable a user to detect particles in the fluid, including blue-green algae particles in the fluid and, specifically, to enhance the accuracy and sensitivity of such detection.

The flow chamber 15 includes an inlet 20 for receiving the particle-containing fluid to be observed, and an outlet 25 through which the fluid passes out of the How chamber 15 after imaging functions have been performed. (For the purpose of describing an example of the present invention, the fluid is a flowing fluid. The system 10 may alternatively be used for particle detection in a non-flowing fluid.) The flow chamber 15 is a low fluorescence structure. That is, it may be fabricated of a material that does not readily fluoresce, including, for example, but not limited to, microscope glass or rectangular glass extrusions. The flow chamber 15 may be circular or rectangular in shape. The flow chamber 15 defines a channel 15a through which the fluid flows at a predetermined selectable rate. The channel 15a may be of rectangular configuration. The length and width of channel 15a are selected to roughly match the field of view of the imaging and fluorescence optics 35. This keeps all of the particles in the fluid in the flow chamber 15 in focus, removing the need for a focusing sheath flow, and thereby enabling accurate counting of cells while retaining imaging capability. This arrangement of the flow chamber 15 and the flow channel 15a also eliminates the problems of particle size limitations associated with convention flow cytometer nozzles. The inlet 20 of the flow chamber 15 is connectable to a fluid source and the outlet 25 is connectable to a downstream means for transferring the fluid away from the flow chamber 15. It is to be understood that the specific design of the flow chamber 15 may vary from the particular example design described herein without deviating from the applicable features of the present invention.

Figure 3:
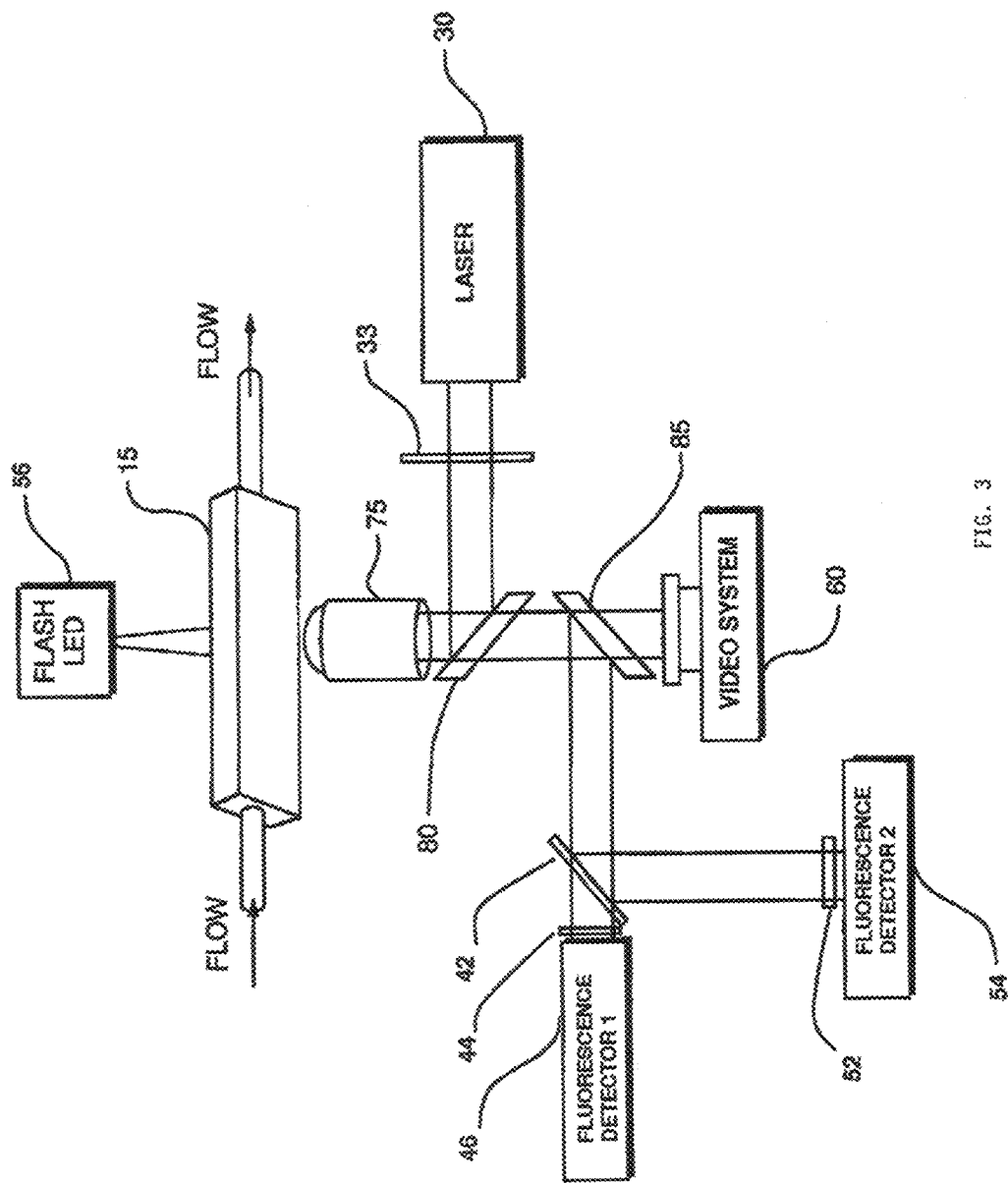
FIG. 3 is a detailed schematic illustration of the plurality of detectors and associated filters for capturing distinct fluorescence characteristics of captured images of particles within a flowing fluid.

With reference to FIGS. 1 and 3, the light source 30 is used to generate fluorescence and scatter excitation light which is passed through the imaging and fluorescence optics 35 to the flow chamber 15, resulting in particle fluorescence and/or light scatter. The light source 30 may be a LASER 30 with an excitation filter 33. The LASER 30 may be, but is not limited to being, a 532 nanometer (nm) solid state model laser available from an array of manufacturers known to those of skill in the art. The excitation filter 33 should at least have the characteristic of being able to transmit light at the wavelength of light generated by the LASER 30 +/−30 nm. An example of a suitable form of the excitation filter 33 is a D633/20× filter of the type that can be used with a 633 nm LASER available from Chroma Technologies of Rockingham, Vt. US; those of skill in the art will recognize that other suitable filters may be employed for the excitation filter 33. Emission filter 80 should at least have the characteristic of being able to transmit light at wavelengths longer than the wavelengths of light generated by the LASER 30. An example of a suitable form of the emission filter 80 is a 650DCLP longpass filter of the type that can be used with a 633 nm LASER. A filter such as emission filter 80 can also be obtained from Chroma Technologies.

With continuing reference to FIG. 3, any particle fluorescence emissions from the flow chamber 15 that have a wavelength of 650 to 900 nm are detected by the detection system 40. The imaging optics 35 include a microscope objective 75 to image the particle flow onto the image capturing system 60, focus fluorescence excitation light from the LASER 30 onto the flow chamber 15 and focus the resulting particle fluorescence onto dichroic mirror 42 of the detection system 40. The dichroic mirror 42 is selected and arranged to pass light longer than approximately 680 nm to first emission filter 44, which further filters the light and passes light wavelengths longer than 700 nm to 900 nm to first fluorescence detector 46. Light of wavelengths shorter than approximately 680 nm, which is reflected off of the dichroic mirror 42, is further filtered by second emission filter 52 to 650 nm+/−5 nm and then passes to second fluorescence detector 54.

Each of the first fluorescence detector 46 and the second fluorescence detector 54 preferably includes a high sensitivity photomultiplier tube (PMT). The PMTs should at least have the characteristic of being sensitive to the fluorescence emissions desired. An example of a suitable form of a PMT is the H9656-20 model available from the Hammamatsu Company of Bridgewater, N.J. US. Those of skill in the art will recognize that other equivalent PMTs may be employed for the detectors 46/54. An example of a suitable form of the first emission filter 44 and the second emission filter 52 is a 700 nm longpass and 650/10 emission filter available from Chroma Technologies of Rockingham, Vt. US. Those of skill in the art will recognize that other suitable filters may be employed for the emission filters 44/52.

With reference to FIG. 1, output from the detectors 46/54 is processed by detection electronics 45. Preferably, the detection electronics 45 includes user-adjusted gain and threshold settings which determine the amount of fluorescence or scatter required for the system 10 to acknowledge a passing particle. The detection electronics 45 may be configured to receive input signals and produce output information compatible with the specific needs of the user of the system 10. An example of a suitable electronics system capable of performing the signal activation and output information associated with the detection electronics 45 of the system 10 is the detection electronics described in U.S. Pat. No. 6,115,119, the entire content of which is incorporated herein by reference. Those of ordinary skill in the art will recognize that the specific electronics system described therein may be modified, such as through suitable programming for example, to trigger desired signal activation and/or to manipulate received signals for desired output information.

If a sufficiently fluorescent particle passes through the flow chamber 15a fluorescence signal from each of the detectors 46/54 at their respective detection wavelengths is sent to the detection electronics 45, which then generate one or more trigger signals that are transmitted to the computing device 65. The computing device 65 is programmed to store the information received from the detection electronics 45 and to make calculations associated with the particles detected. For example, but not limited thereto, the computing device 65 may be programmed to provide specific information regarding the fluorescence of the detected particles, the shape of the particles, dimensions of the particles, and specific features of the particles. The computing device 65 may be any sort of computing system suitable for receiving information, running software programs on its one or more processors, and producing output of information, including, but not limited to images and data, that may be observed on a user interface.

The detection electronics 45 may also be coupled, directly or indirectly through the computing device 65 to the backlighting generator 50. In particular, the detection electronics 45 and/or the computing device 65 may include an arrangement whereby a user of the system 10 may alternatively select a setting to automatically generate a trigger signal at a selectable time interval. The trigger signal generated produces a signal to activate the operation of the backlighting generator 50 so that a light flash is generated. Specifically, the backlighting generator 50 may be a Light Emitting Diode (LED) or other suitable light generating means that produces a light of sufficient intensity to backlight the flow chamber 15 and image the passing particles. The very high intensity LED flash may be a 670 nm LED flash, or a flash of another other suitable wavelength, which is flashed on one side of the flow chamber 15 for 200 μsec (or less). At the same time, if it is desired, the optional image capturing system 60 positioned on the opposing side of the flow chamber 15 may be activated to capture an instantaneous image of the particles in the fluid as "frozen" when the high intensity flash occurs.

The optional image capturing system 60 is arranged to either retain the captured image, transfer it to the computing device 65, or a combination of the two. The image capturing system 60 includes characteristics of a digital camera or an analog camera with a framegrabber or other means for retaining images. For example, but in no way limiting what this particular component of the system may be, the image capturing system 60 may be, but is not limited to being, a CCD firewire, a CCD USB-based camera, or other suitable device that can be used to capture images and that further preferably includes computing means or that may be coupled to computing means for the purpose of retaining images and to manipulate those images as desired. The computing device 65 may be programmed to measure the size and shape of the particle captured by the image capturing system 60 and/or store the data for later analysis.

The images captured by the image capturing system 60 and stored with the computing device 65 may be used to analyze the particles in the fluid and compare them to known images of particles including, specifically, blue-green algae. When a trigger is generated (i.e., a fluorescent or light scattering particle is detected), software scans the resulting image, separating the different particle sub-images in it. The area of each particle is measured by summing the number of pixels in each particle image below a software selected threshold and multiplying the result by the equivalent physical area of a pixel. This computed area of the particle is stored in a spreadsheet-compatible file along with other properties of the particle, e.g., its measured peak fluorescence, time of particle passage, and the location of the particle in the image. The sub-image of each particle is copied from the chamber image and saved with other sub-images in a collage file. Several of these collage files may be generated for each system experiment. A special system file is generated, containing the collage file location of each particle sub-image, particle size, fluorescence and time of particle passage.

The software is written to generate two data review modes: (1) image collage and (2) interactive scattergram. In the image collage mode, the user may review a series of selectable sub-images in a collage file. Reviewing these files allows the user to identify particle types, count particles, or study other features. In interactive scattergram mode, data are presented to the user as a dot-plot; e.g., a graph of particle size vs. particle fluorescence or light scatter. If the user selects a region of the scattergram, images of panicles having the characteristics plotted in that region are displayed on a display of the computing device 65, allowing the user to study particle populations and to examine images of particles with specific sixes or fluorescence, such as cells of a specific type. Because a spreadsheet compatible file is generated for each review, the user may also review the data with a spreadsheet program. This information allows the user to readily generate cell counts and fluorescence or scatter and size distribution histograms for each sample. This file also contains the location of each particle in the original image which is used to remove redundant data from particles that have become attached to the flow chamber 15.

Figure 4:
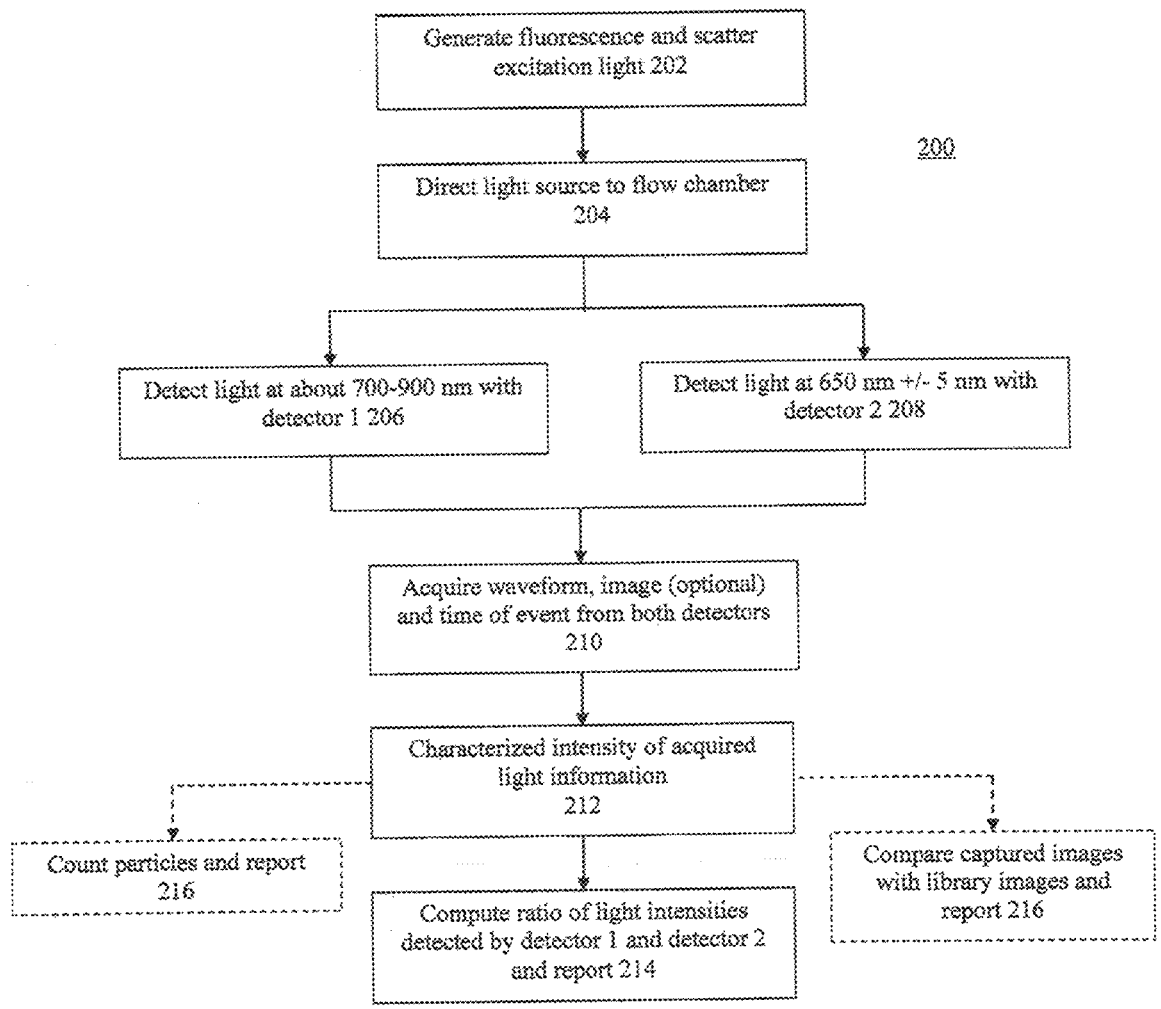
FIG. 4 is a flow diagram representing steps to be carried out in a first method of the present invention using the computing device and associated programming described.

As represented in FIG. 4, a method 200 of the present invention embodied in one or more computer programs, includes steps associated with storing and analyzing information captured with the system 10 of the present invention. In the first step, step 202, the LASER 30 and imaging and fluorescence optics 35 generate fluorescence and scatter excitation light, which is directed to the flow chamber 15 within which a fluid to be monitored passes, step 204. The detection system 40 including the detection electronics 45 is used to detect fluorescence information and, separately, signals associated with the light waveforms scattered from particles in the flow chamber 15 at two distinct wavelengths, steps 206 and 208. The detected signal data, including distinct fluorescence information any optional imaging data that may be acquired, are transferred to the computing device 65 for storage and analysis, step 210. The captured signal data are characterized based on intensities at the respective designated wavelengths, in addition to other information of interest, step 212. The ratio of fluorescence intensities for a given particle at the distinct wavelengths is then calculated as a means of distinguishing the phycocyanin and chlorophyll b features represented of blue-green algae particles in the fluid and that information may be reported in a visual manner, step 214. For example, the information may be presented in graphic representations, spreadsheet lists, or combinations thereof. Optionally, the acquired image information may be used to count the number of particles in the fluid sample observed and reported, step 216.

Figure 5:
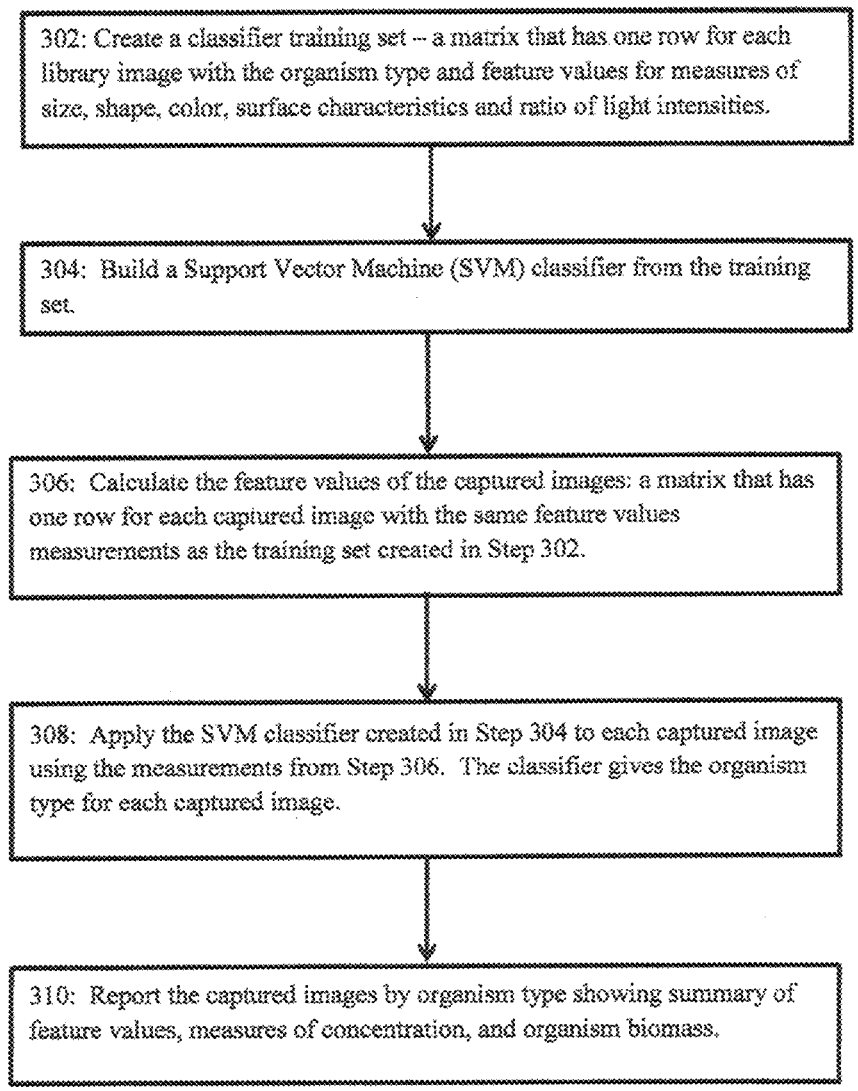
FIG. 5 is a flow diagram representing steps to be carried out in a second method of the present invention using the computing device and associated programming described.

After a data gathering run has been completed, the data and images are processed using method 300 with the steps shown in FIG. 5. Initially, the user creates a classifier training set for each library image of known particles, including known organisms, step 302. Then a Support Vector Machine classifier is built in step 304. The SVM classifier is a supervised learning model with one or more associated learning algorithms that analyze data and recognize patterns, used for classification and regression analysis. Given a set of training examples, each marked for belonging to one of two categories, an SVM training algorithm builds a model that assigns new examples into one category or the other, making it a non-probabilistic binary linear classifier. In general, an SVM model is a representation of the examples as points in space, mapped so that the examples of the separate categories are divided by a clear gap that is as wide as possible. New examples are then mapped into that same space and predicted to belong to a category based on which side of the gap they fall on. A SVM classifier for the present invention can be built using the method described in V. Vapnik, "The Nature of Statistical Learning Theory, New York; Springer-Verlag, 1995, or in Cortes, C.; Vapnik, V. (1995); "Support-vector networks". Machine Learning 20 (3); 273. For purposes of the present invention, the SVM classifier may be built by one of skilled in the art using the data gathered with the imaging system described herein and characterizes the images of particles, such as organisms, for example, accordingly.

Figure 6:
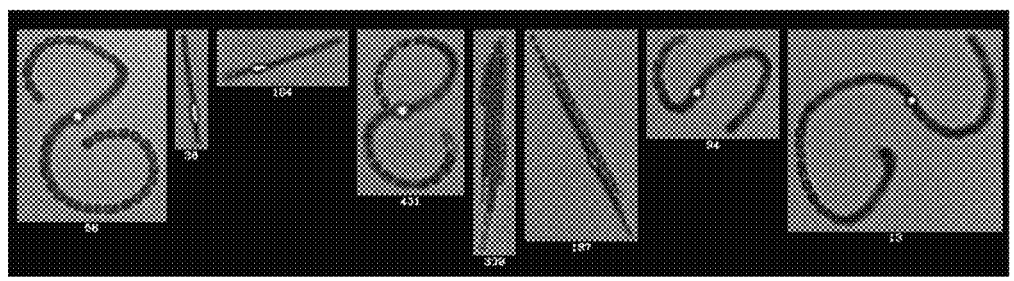
FIG. 6 depicts several example images of blue-green algae captured and classified using the system of the present invention.

With continuing reference to FIG. 5, in step 306, the program is configured to calculate the feature values of the captured images. Next in step 308, the SVM classifier is applied to each captured image using the measurements from step 306 and, optionally, a report is generated in step 310. FIG. 6 presents example images of filamentous blue-green algae cyanobacteria *Anabaena*, which may be classified to identify suspect particles.

It is to be understood that the computing device 65 used to gather the captured image information and to perform calculations and observe features of the captured image information may be associated with local or remote computing means, such as one or more central computers, in a local area network, a metropolitan area network, a wide area network, or through intranet and internet connections. The computing device 65 may include one or more discrete computer processor devices. The computing device may include computer devices operated by a centralized administrative entity or by a plurality of users located at one or more locations.

The computing device 65 may be programmed to include one or more of the functions of the system 10. The computing device 65 may include one or more databases including information related to the use of the system 10. For example, such a database may include known images of example particles of interest. The database may be populated and updated with information provided by the user and others.

The steps of the methods 200 and 300 described herein and additional steps not specifically described with respect to FIGS. 4 and 5 but related to the use of the system 10 may be carried out as electronic functions performed through the computing device 65 based on computer programming steps. The functions configured to perform the steps described herein may be implemented in hardware and/or software. For example, particular software, firmware, or microcode functions executing on the computing device 65 can provide the trigger, image capturing and image analysis and fluorescence or scatter signal analysis functions. Alternatively, or in addition, hardware modules, such as programmable arrays, can be used in the devices to provide some or all of those functions, provided they are programmed to perform the steps described.

The steps of the methods 200 and 300 of the present invention. Individually or in combination, may be implemented as a computer program product tangibly as computer-readable signals on a computer-readable medium, for example, a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual Basic, C, or C++, Fortran, Pascal, Eiffel, Basic, COBOL, and the like, or any of a variety of combinations thereof. The computer-readable medium on which such instructions are stored may reside on one or more of the components of system 10 described above and may be distributed across one or more such components. Further, the steps of the method represented in FIG. 4, may be performed in alternative orders, in parallel and serially.

The system 10 of the present invention allows much greater sensitivity to particles, including particles of blue-green algae due to multiple fluorescence measurements for individual particles, and the optional verification of particles with image capture. One important use for this invention is the monitoring of drinking water that would otherwise become foul tasting due to the presence of blue-green algae. As previously described, the invention is carried out by installing a phycocyanin and chlorophyll b fluorescence filter set, first filter 44 and second filter 52, respectively, into a detection system such as, but not limited to, an imaging flow cytometer system, and configuring the computing device, through software to compute the ratio of the two channels of fluorescence and then using known imaging capabilities to count the blue-green algae particles, if desired.

One or more example embodiments to help illustrate the invention have been described. Nevertheless, it will be understood that various modifications may be made without departing from the spirit and scope of the invention. Accordingly, other embodiments are within the scope of the claims appended hereto.

What is claimed is:

1. A system for analyzing particles in a fluid, the system comprising:
    a flow chamber for receiving a sample of fluid to be analyzed;
    one or more detectors positioned to detect two different ranges of fluorescence produced by particles in the fluid in said flow chamber, said detectors generating a trigger signal whenever fluorescence is detected;
    a classifier training set containing organism type and feature values, wherein the classifier training set comprises a matrix having at least one row of each image of a library of images with particle type and at least another row of feature values for particles; and a support vector machine classifier training set including related particle images, wherein feature values of captured images are calculated and the support vector machine classifier training set is applied to captured images to classify the particle associated with each image.

2. The system of claim 1 further comprising a light source arranged to direct excitation light onto said flow chamber.

3. The system of claim 2 further comprising a high intensity light source positioned to backlight said flow chamber in response to said trigger signal.

4. The system of claim 1 further comprising a video system positioned to image particles in the fluid passing through said flow chamber; and imaging optics for focusing light from said flow chamber onto said video system, wherein said video system images particles in the fluid passing through said flow chamber in response to said trigger signal, wherein the video system includes means for storing and analyzing particle images captured by said video system.

5. The system of claim 4 wherein the fluid is flowing through said chamber and said video system automatically images particles in the fluid passing through said flow chamber at a predetermined time interval.

6. The system of claim 4 wherein said video system includes a digital camera or a video camera and a framegrabber.

7. The system of claim 1 wherein the flow chamber includes a flow channel configured such that its dimensions match the field of view associated with the detectors.

8. The system of claim 1 wherein the feature values of the matrix comprise measures of size, shape, color, surface characteristics and ratio of light intensity.

9. A method for analyzing particles in a fluid, the method comprising the steps of:

directing a sample of fluid to be analyzed into a flow chamber having a chamber depth;

detecting two different ranges of fluorescence produced by particles in the fluid in said flow chamber;

storing fluorescence data obtained in said detecting step;

creating a classifier training set using organism type and feature values, wherein the classifier training set comprises a matrix having at least one row of each image of a library of images with particle type and at least another row of feature values for particles;

building a support vector machine classifier training set related to particle images;

calculating feature values of captured images; and applying the support vector machine classifier training set to captured images to classify the organism associated with each image.

10. The method of claim 9 further comprising the steps of:

using imaging optics to focus light from said flow chamber onto a video system;

imaging particles in the fluid in said flow chamber with said video system; and analyzing images captured by said video system.

11. The method of claim 10 wherein the step of imaging particles in the fluid includes:

directing excitation light onto said flow chamber;

generating a trigger signal whenever fluorescence is detected; and imaging the particles in the fluid in response to said trigger signal.

12. The method of claim 10 wherein the step of analyzing images captured by said video system includes determining the size of each imaged particle.

13. The method of claim 10 wherein the step of analyzing images captured by said video system includes determining the peak fluorescence of each imaged particle.

14. The method of claim 10 wherein the fluid is flowing in said flow chamber and the step of analyzing images captured by said video system includes determining the time of particle passage for each imaged particle.

15. The method of claim 14 wherein the step of analyzing images captured by said video system includes determining the image location for each imaged particle.

16. The method of claim 10 wherein the step of analyzing images includes:

displaying an interactive scattergram comprising a graph plotting particle size against particle fluorescence on a display;

selecting a particular region of said scattergram; and displaying the images in said selected region on said display.

17. The method of claim 9 wherein the feature values of the matrix comprise measures of size, shape, color, surface characteristics and ratio of light intensity.

* * * * *